United States Patent [19]

Huland

[11] Patent Number: 5,474,903
[45] Date of Patent: Dec. 12, 1995

[54] PROCESS FOR THE QUANTITATIVE DETERMINATION OF PROSTATE SPECIFIC ANTIGEN

[76] Inventor: Edith Huland, Barkenkoppel 8, Hamburg 22381, Germany

[21] Appl. No.: 136,381

[22] Filed: Oct. 13, 1993

[30] Foreign Application Priority Data

Oct. 21, 1992 [EP] European Pat. Off. ............. 92117983

[51] Int. Cl.$^6$ .................... G01N 33/574; G01N 33/53
[52] U.S. Cl. ................. 435/7.23; 435/7.92; 435/7.94; 436/518; 436/64; 436/813
[58] Field of Search .................... 436/518, 813, 436/64; 435/7.9, 7.92, 7.93, 7.94, 7.95, 962, 967, 287, 289, 290, 291, 7.23; 422/63, 68.1

[56] References Cited

U.S. PATENT DOCUMENTS

| | | | |
|---|---|---|---|
| Re. 33,405 | 10/1990 | Chu et al. | 530/350 |
| 4,140,753 | 2/1979 | Edgington et al. | 424/88 |
| 4,711,839 | 12/1987 | Singhal | 435/4 |
| 5,244,786 | 9/1993 | Picone et al. | 435/7.9 |

FOREIGN PATENT DOCUMENTS

| | | |
|---|---|---|
| 0153382 | 8/1985 | European Pat. Off. . |
| 0196845 | 8/1986 | European Pat. Off. . |
| 9212430 | 7/1992 | WIPO . |

OTHER PUBLICATIONS

Lange, P. H., et al. The value of Serum prostate specific antigen determinations before & after radical prostatectomy. Journal of Urology 141:873–879, 1989.

Tachibana, C. F. et al. High prevalence of e antigen among healthy blood donors carrying hepatitis B surface antigen in Japan. Vox Sang 32:296–299, 1977.

Tietz, N. W. Clinical Chemistry. Philadelphia: W B Saunders, 1986. pp. 27, 215–229.

Zubay, G. L., Biochemistry Reading, Mass: Addison-Wesley, 1983. pp. 478–479.

Graves, et al, "Ultrasensitive Radioimmunoassay fo Prostate Specific Antigen", Clinical Chemistry, vol. 38, No. 5, 1992, p. 735.

Graves, et al, "Comparison of a Polyclonal and Monoclonal Immunoassay for PSA: Need For An International Antigen Standard", The Journal of Urology, vol. 144, No. 6, Dec. 1990 p. 1516.

Primary Examiner—Toni R. Scheiner
Assistant Examiner—Yvonne Eyler
Attorney, Agent, or Firm—Richard S. Roberts

[57] ABSTRACT

The invention concerns a process for the quantitative determination of prostate specific antigen in a patient sample, with a predetermined weight or volume, through analysis. A patient sample undergoes a freeze concentration, is analyzed by standard quantitative analysis methods such as immunoassay techniques, and then the substance content is calculated back to the original sample volume or weight.

9 Claims, 1 Drawing Sheet

PROCESS FOR THE QUANTITATIVE DETERMINATION OF PROSTATE SPECIFIC ANTIGEN

BACKGROUND OF THE INVENTION

The invention concerns a process for the quantitative determination of illness specific antigens, in particular prostate specific antigens, as well as an apparatus for conducting this process.

Prostate specific antigen (PSA) is a tissue specific glycoprotein which can only be found in the prostate gland and its secretions. Because of the tissue specificity of PSA, it is well known to be a unique indicator for the prostate function as described by Hara M., and Kimura, H.: Two prostate-specific antigens, gamma-semino-protein and beta-microsemino-protein. J. Lab. Clin. Med. 1989; 113: 541–48; Graves, H. C. B., Kamarei, M., and Stamey T. A.: Identity of prostate specific antigen and the semen protein p30 purified by a rapid chromatography technique, J. Urol. 1990; 144:1510–5; and Sensabaugh, G. F., and Blake, E. T.: Seminal plasma protein p30: Simplified purification and evidence for identity with prostate specific antigen, J. Urol. 1990; 144: 1523–26. On the strength of these findings, PSA is therefore a particularly useful indicator in controlling patients after radical prostatectomy, and determining whether they suffer any further appearance of their prostate cancer. This because the operative intervention should have removed the entire prostate tissue and therewith also the possible source for releasing prostate specific antigen. In patients with a prostate cancer, in whom, through histological examination the cancer has been proven to be limited to the prostate organ, the value of PSA after radical prostatectomy falls under the detection level of the presently available immunoassays in 80–92% of the cases. A further increase in the PSA value is the earliest available indicator for a further appearance of the cancer after a complete prostatectomy. In this regard see Stamey, T. A., Yang, N., Hay, A. R., McNeal, J. E., Freiha, F. S., and Redwine, E.: Prostate-specific antigen as a serum marker for adenocarcinoma of the prostate. N. Engl. J. Med. 1987; 317:909–16. Oesterling, J. E., Chan, D. W., Epstein, J. I., Kimball, A. W., Bruzek, D. J., Rock, R. C., Brendler, C. B., and Walsh, P. C.: Prostate specific antigen in the preoperative and postoperative evaluation of localized prostatic cancer treated with radical prostatectomy. J. Urol. 1988; 139:766–72. Oesterling, J. E.: Prostate specific antigen: A critical assessment of the most useful tumor marker for adenocarcinoma of the prostate, J. Urol. 1991; 145:907–23. Lightner, D. J., Lange, P. H., Reddy, P. K., and Moore L.: Prostate specific antigen and local recurrence after radical prostatectomy. J. Urol. 1990; 144:921–26.

The presently available immunoassays for PSA can detect a PSA serum value of between 0.3 and 50 ng/ml. The sensitivity of the two leading commercially available immunoassays for PSA has a minimum analytical sensitivity of from 0.6 –0.8 ng/ml PSA. In this regard see Graves, H. C. B., Wehner, N., and Stamey T. A.: Comparison of a polyclonal and monoclonal immunoassay for PSA: Need for an international antigen standard, J. Urol. 1990; 144: 1516–22. In cases of a complete removal of a normal prostate, which became available by cystoprostatectomies due to causes other than prostate cancer, postoperative PSA values of less than 0.3 ng/ml have been found through the Yang Pros-check PSA. See Stamey, T. A., Kabalin, J. N., McNeal, J. E., Johnstone, I. M., Freiha, F., Redwine, E. A., and Yang, N.: Prostate specific antigen in the diagnosis and treatment of adenocarcinoma of the prostate, 11. Radical prostatectomy treated patients, J. Urol. 1989; 141:1076–83; Lange P. H., Ercole, C. J., Lightner, D. J., Fraley, E. E., and Vessella, R.: The value of serum prostate specific antigen determinations before and after radical prostatectomy, J. Urol. 1989; 141: 873–79; Hudson, M. A., Bahnson, R. R., and Catalona, W. J.: Clinical use of prostate specific antigen in patients with prostate cancer. J. Urol. 1989; 142: 111–17.

At this time an intensive effort is being made to find a sensitive immunoassay which detects a lower PSA level since such would be extraordinarily helpful for an early diagnosis of a recidivism of the prostate cancer in patients after radical prostatectomy. These ultrasensitive assays have a working area of from 0.1–1.2 ng/ml and thereby improve the analytical sensitivity by about three fold. Difficulties go along with such ultrasensitive assays. For example, the PSA calibrators in the lower regions (<0.5 ng/ml) are not stabile if they are stored at about 4° C., so that a calibration curve must be newly produced every day since a higher calibrator standard (for example an 8 ng/ml PSA calibrator) is weakened. The several day incubation times are expensive and demand strict temperature and bacteria contamination controls. See Graves, H. C. B., Wehner, N., and Stamey, T. A.: An ultrasensitive radioimmunoassay for prostate specific antigen. 1992, Clin. Chem.

The present invention therefore provides an improvement on the known type of processes and avoids the described disadvantages. It is generally useful with illness specific antigens; is technically simple in all laboratories; and in addition can be combined with other sensitivity improvement processes.

The process of the invention is principally based on a serum sample which is reduced through freeze drying to ⅕, ¹⁄₁₀ or ¹⁄₂₀ of its original volume. The volume of the extracted sample and the volume after reduction are determined. This factor is taken into consideration by the concentration calculation. The thusly reduced sample, which is considerably diminished in water content, but after as before, contains the prostate specific antigen in the same quantitative amount as the extracted sample, can then be analyzed in the customary way, and in particular, measured with traditional, commercially available immunoassays. Initial low concentrations henceforth appear in a measurable area of the immunoassay by the thusly obtained concentration. After the sample is measured with standard processes as before, the concentration of the sample from the extracted serum amount is determined by calculation.

To be sure, concentration through freeze drying is not fundamentally new, indeed, freeze drying is done regularly and frequently in order to raise the stability of proteins, tissues or other biological products, and in this manner makes the corresponding reagents durable and storable. In this way controls or reagents are treated in immunologically standard test processes. Another known and established process for freeze drying stems from the desire for weight or space savings. If sample water is removed, without changing its composition in other respects, it can be transported easier, and a complete, problem free reconstitution with water is possible. The principal of freeze drying can therefore also offer a considerable advantage from the viewpoint of storage (compare, for example U.S. Pat. No. 4,994,375). The stability of substances in long term storage can in general be maintained very well by freeze drying, and for the most part better, but at least as well as deep freeze storage, so that such a consideration of stability preservation likewise represents an important area of use for freeze drying.

New and surprising, is that despite the long and universal use of freeze drying measures, a process which uses such an effective means of concentration has not been used to attain an improved sensitivity in the measurement of, for example tumor indicators, such as illness specific antigens. Until now an improvement of the sensitivity of an analytical method predominantly would involve a change in the assay method. The reduction of samples, in order to thereby raise the concentration of the corresponding indicators, and to thereby convert the sample from background noise to the measurable area has heretofore not been done and also has not been reported in the literature.

Also of particular importance is an apparatus for conducting the process, which is characterized by a combination of several known devices. These include an apparatus for the determination of sample weight and/or volume, before and after freeze concentration; a calculator for the determination of the resulting concentration factors therefrom, as well as for back calculating the determined value of the extraction weight and volume of the sample from the patient; in conjunction with devices for conducting the freeze concentration itself and the final analysis of the immunological assays. Through a combination of these devices, a further automation of the described process for sensitivity improvement can be attained.

Therefore, according to the invention a process for the quantitative proof of prostate specific antigens by customary immunoassays is produced, which makes reliable analyses possible in low concentration areas. This process is characterized in that in the first instance a sample undergoes a freeze concentration and then thereafter an analysis or a standard assay is conducted, and that the therefrom resulting product is calculated back to its original sample volume.

SUMMARY OF THE INVENTION

The invention provides an improved process for the quantitative determination of antigen in a sample of patient serum of a predetermined volume or weight which comprises subjecting the patient serum sample to a concentration step to reduce the water content thereof, analyzing the concentrated sample to determine the antigen content thereof, and calculating back the antigen content of the original patient serum sample.

The invention also provides an improved process for the determining the quantity of a substance, particularly a biological material, in a biological sample which comprises subjecting the sample to a concentration step to reduce the water content thereof, and then analyzing the concentrated sample to determine the amount of the substance therein.

The invention further provides an apparatus for the quantitative determination of antigen in a sample of patient serum of a predetermined volume or weight which comprises means for subjecting the patient serum sample to a concentration step to reduce the water content thereof, means for analyzing the concentrated sample to determine the antigen content thereof, and means for calculating back the antigen content of the original patient serum sample.

DETAILED DESCRIPTION OF THE PREFERRED EMBODIMENT

Figure 1:
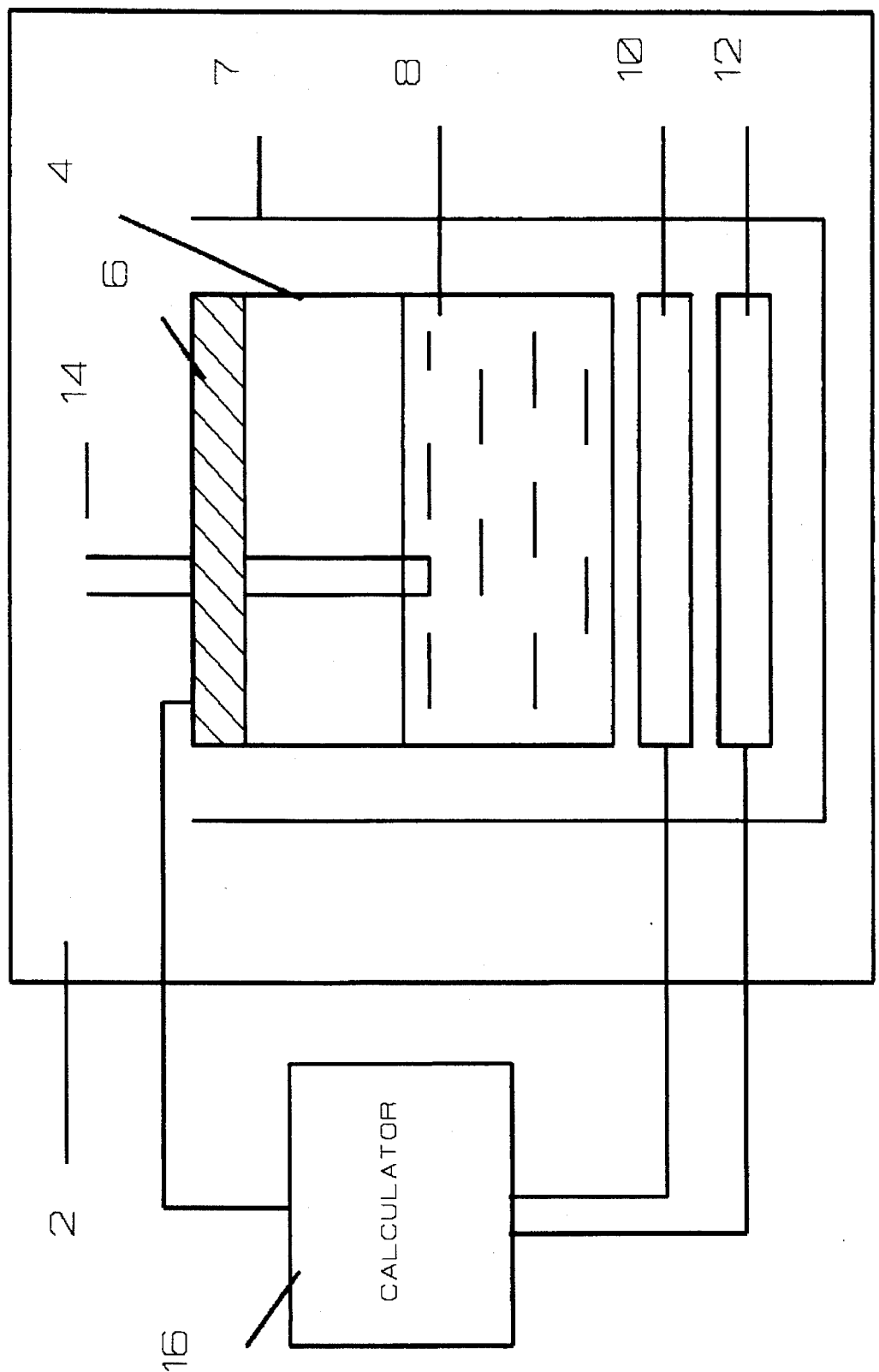
FIG. 1 shows a schematic representation of an apparatus useful for conducting the process of the present invention.

In conducting the process of the present invention, one first obtains a serum sample which contains the substance, such as an antigen to be investigated from a patient. The weight and/or volume of the sample is measured. In a typical investigation, two, three or four such samples are measured. The water content of the samples are then reduced to concentrate the sample. This is done by drying, such as by freeze drying. As an example, 10 ml of the serum sample under study, as well respectively, an exemplary 10 ml of a corresponding control and calibration standard are deep frozen and treated in a freeze drying unit for several hours until the weight of the sample is reduced to 5%, 10%, 20%, 30% or 50% of its original volume. The volume and/or weight measurement is done very exactly both before and after freeze drying. Hereby the factor is determined, about whether the subsequently measured value must be corrected, in order to obtain the concentration of the extracted quantity. For the facilitation of this procedure, a complete freeze drying or almost complete freeze drying can be done with an associated redissolution to a defined total volume or total weight, for example 1 ml or 2 ml. The dissolution of the highly concentrated serum lyophilisate is eased through a short incubation of 15–30 minutes in a 37° C. water bath. Attention must be paid to an exact and thorough blending of all the serum ingredients. The sample obtained in this way can then be measured by known quantitative analysis methods, for example, in customary assay systems such as the Yang Pros-check, Hybritech Tandem PSA assay, IMx PSA assay, and others. The thusly conducted reduction leads to a concentration of the sample by a factor of 2 to 20 and thereby also to a corresponding sensitivity improvement. Non-immunologic analysis methods can also be used.

An example of the inventive sample measurement is presented in Table 1.

TABLE 1

| Reduction | Measured Value (ng/ml) | Theoretical Value (ng/ml) | Post-Freeze Concentration 10 ml to 2 ml (ng/ml) | Back Calculated Concentration to 10 ml |
|---|---|---|---|---|
| Unreduced | 1.23 | 1.2 unreduced | 5.90  $\bar{x} = 5.91$ | 1.18 ng/ml |
|  | 1.13 |  | 5.97 |  |
|  | 1.21 |  | 5.87 |  |
| 1:1 | 0.57 | 0.6 | 2.65  $\bar{x} = 2.58$ | 0.51 ng/ml |
|  | 0.51 |  | 22.51 |  |
|  | 0.56 |  | 2.58 |  |

TABLE 1-continued

| Reduction | Measured Value (ng/ml) | Theoretical Value (ng/ml) | Post-Freeze Concentration 10 ml to 2 ml (ng/ml) | Back Calculated Concentration to 10 ml |
|---|---|---|---|---|
| 1:10 | 0.02 | 0.06 | 0.21 $\bar{x} = 0.19$ | 0.04 ng/ml |
|  | 0.00 |  | 0.17 |  |
|  | 0.00 |  | 0.19 |  |
| "0" serum | 0.00 | 0 | 0.00 | 0 ng/ml |
|  | 0.00 |  | 0.00 |  |
|  | 0.00 |  | 0.00 |  |

In this example, for a sample measurement, 55 ml serum with a PSA value of 1.2 ng/ml is produced and measured in various reduction steps with a null serum (comprising a pooled female serum containing negligible PSA). Column 1 provides the various reductions of the serum. Column 2 shows the measured value resulting from the analysis without the inventive treatment. Column 3 shows the theoretical value, as calculated from the reduction which must result. Column 4 shows the measured value, after freeze concentration from 10 ml to 2 ml with the corresponding enzyme immunoassay. Column 5 provides the ascertained concentration through back calculation to 10 ml. In the given example, a commercially available and widely distributed assay system was used, namely, the IMx PSA Immunoassay from Abbott, the so called Microparticle Enzyme Immunoassay MEIA. In this table, line 4 clearly shows that at a 1:10 reduction of the original serum, the usual assay without pretreatment of the patient sample only shows a 0 value even in a threefold testing. Freeze concentration allows a surer measured value to be determined, wherein by a back calculation of the concentration, a reliable, positive finding is determined. On the other hand, the "0" serum (female serum without PSA content) also remains completely negative after sample treatment by freeze drying concentration.

The sensitivity of the PSA measurement can therefore be raised by a heretofore unreached factor, and by use of customary analytical or immunoassay processes. The sample preparation can by all means also be combined with super sensitive measurement processes so that an additional improvement is made possible in the lower measurement areas in heretofore unreachable regions.

A further concentration of the sample through freeze drying is fundamentally possible. Under certain circumstances, in an intermediate step, an essentially irrelevant solid in the serum must be separated out in order to avoid a distinct viscousness of the sample. This can be attained, for example by a targeted removal of albumin.

The inventive process can also be carried out with other substances which are provided in a low concentration in sample volumes. By this means, tumor indicators, as well as other substances which are present in very low concentrations in bodily fluids can be detected with a high degree of sensitivity. Measurably raising the concentration of patient samples also allows, with the help of the claimed process, detection of such other illness specific antigens as, for example Interleukin-2. Also, this is a substance which is not normally found in serum, but which can increase with illnesses, for example in the rejection of a transplanted foreign kidney. In addition there is also the possibility, through the improvement of detection sensitivity, to make an earlier diagnosis and to commence therapy earlier, which is of considerable benefit to the patient. The method can also be used to measure traces of toxic, infectious or other biological material in biological samples. For example, it could be used to detect traces of vitamins or medication in animal urine or tissue extracts.

It would at once be clear to one skilled in the art that the inventive process would be useful not only for the described cases of PSA and interleukin-2, but would also be generally useful for all illness specific antigens. With many ailments, the corresponding illness specific antigens are, after a first therapy or in the early phases, initially in the non-measurable areas, and one presumes therefrom, that the patient is healthy or healed. The first occurrence in a progression of the disease, is an increase in the amount of the illness specific antigens, and although these could then be detected with customary measurement processes, detection is temporarily delayed. The inventive process goes further in that the antigens in the patient sample, which are in very low concentrations, and therefore lie in the non-measurable or hardly measurable areas of customary assays, are so concentrated, that they are brought into a measurable area for customary measurement processes. Early detection of illness specific antigens can put the doctor in a position to carry out therapy earlier and more effectively. With a few sensitive, robust, illness specific antigens, it is clear to one skilled in the art that the freeze drying process can be substituted by other common drying processes, such as spray drying.

With the inventive process only the side is treated while the immunoassay procedure used is not changed. In this way the process is combinable with all customary measuring processes.

The time factor is insignificant, since it only depends on the time which the freeze drying takes. In the tests the high concentration of other serum ingredients in the reduced sample are not disturbed (in our example IMx PSA assay from Abbott), and the homogeneity leads, surprisingly in fact, to a simple and reliable process for sensitivity improvement. This consideration is fundamentally new and has not yet been used before especially for the case of PSA, although clearly for years an ultrasensitive detection process has been intensively sought.

The following non-limiting examples serve to illustrate the invention.

EXAMPLE 1

Extract a serum probe containing prostate specific antigen (PSA) Weigh the probe. Freeze-dry the probe. Weigh the lyophilized serum probes. Add distilled water to the lyophilized serum to achieve serum probes in the following concentrations: 2 times, 3 times, 4 times and vortex carefully. Measure the concentrated and unconcentrated serum in a standard assay (Abbott, Hybritech)

Interpretation of Lyoconcentration:

Positive:

Any continuous increase in all concentrated samples.

Any continuous increase in the last 2 concentrated samples compared to native serum.

All samples which show a clear positive value in the subsequent assay after concentration.

Suspicious:

Three-times increase in 4-fold concentration compared to native serum.

Negative:

All others.

In this Example, 15 out of 34 positive results of concentrated patient sera after radical prostatectomy are shown below.

| Patient number | Days after Radical PE | PSA-value of Native Serum | PSA-value of Lyoconcentrated Sera | | |
|---|---|---|---|---|---|
| | | | 2-fold | 3-fold | 4-fold |
| 74 | 70 | 0.00 | 0.01 | 0.06 | 0.08 |
| 124 | 551 | 0.00 | 0.02 | 0.04 | 0.06 |
| 95 | 357 | 0.00 | 0.00 | 0.02 | 0.04 |
| 160 | 265 | 0.01 | 0.03 | 0.03 | 0.06 |
| 168 | 81 | 0.01 | 0.02 | 0.02 | 0.03 |
| 184 | 105 | 0.01 | 0.01 | 0.02 | 0.03 |
| 156 | 199 | 0.02 | 0.14 | 0.23 | 0.32 |
| 105 | 91 | 0.03 | 0.12 | 0.12 | 0.13 |
| 211 | 203 | 0.04 | 0.15 | 0.30 | 0.32 |
| 115 | 129 | 0.07 | 0.15 | 0.27 | 0.29 |
| 175 | 378 | 0.13 | 0.23 | 0.38 | 0.50 |
| 208 | 408 | 0.17 | 0.31 | 0.41 | 0.46 |
| 162 | 196 | 0.39 | 0.71 | 0.99 | 1.13 |
| 173 | 64 | 0.69 | 1.32 | 2.02 | 2.44 |
| 210 | 71 | 1.26 | 2.55 | 3.62 | 4.14 |
| n = 34 | x = 219 p. OP-range(d) 39–551 | x = 0.16 range 0.00–1.26 | x = 0.34 range 0.00–2.55 | x = 0.51 range 0.00–3.62 | x = 0.58 range 0.00–4.14 |

EXAMPLE 2

The procedure of Example 1 is repeated and 5 out of 11 suspicious results of concentrated patient sera after radical prostatectomy are shown below.

| Patient number | Days after Radical PE | PSA-value of Native Serum | PSA-value of Lyoconcentrated Sera | | |
|---|---|---|---|---|---|
| | | | 2-fold | 3-fold | 4-fold |
| 70 | 288 | 0.00 | 0.00 | 0.00 | 0.03 |
| 143 | 573 | 0.00 | 0.00 | 0.03 | 0.03 |
| 223 | 59 | 0.00 | 0.00 | 0.00 | 0.03 |
| 79 | 325 | 0.01 | 0.01 | 0.03 | 0.03 |
| 214 | 204 | 0.01 | 0.01 | 0.01 | 0.08 |
| n = 11 | x = 247 p. OP-range(d) 59–573 | x = 0.01 range 0.00–0.03 | x = 0.00 range 0.00–0.01 | x = 0.01 range 0.00–0.03 | x = 0.04 range 0.02–0.08 |

EXAMPLE 3

The procedure of Example 1 is repeated and 5 out of 91 negative results of concentrated patient sera after radical prostatectomy are shown below.

| Patient number | Days after Radical PE | PSA-value of Native Serum | PSA-value of Lyoconcentrated Sera | | |
|---|---|---|---|---|---|
| | | | 2-fold | 3-fold | 4-fold |
| 164 | 69 | 0.02 | 0.01 | 0.01 | 0.01 |
| 190 | 408 | 0.02 | 0.00 | 0.00 | 0.00 |
| 193 | 95 | 0.03 | 0.04 | 0.03 | 0.02 |
| 198 | 244 | 0.01 | 0.02 | 0.02 | 0.02 |
| 200 | 317 | 0.00 | 0.01 | 0.01 | 0.00 |
| n = 33 | x = 219 p. OP-range(d) 35–1183 | x = 0.03 range 0.00–0.11 | x = 0.02 range 0.00–0.09 | x = 0.02 range 0.00–0.08 | x = 0.02 range 0.02–0.08 |
| n = 48 | x = 209 p. OP-range(d) 36–1416 | x = 0.00 range 0.00–0.00 | x = 0.00 range 0.00–0.00 | x = 0.00 range 0.00–0.00 | x = 0.00 range 0.00–0.00 |

The data above in Examples 1, 2 and 3 show the results of 126 measurements with 2-fold, 3-fold and 4-fold concentration. After lyoconcentration, these samples are sorted according to the definition as positive (n=34), suspicious (n=11) and negative (n=91) and in the tables only a few of those are shown, i.e. 15 of 34 positives, 5 of 11 suspicious and 5 of 81 negatives. However, from these date, it is clear that we can identify 34 of 136 measurements as positive. In contrast, with standard analysis alone, only 14 patients could be identified as positive.

EXAMPLE 4

The procedure of Example 1 is repeated using measurements of PSA values (Abbott IMX) in lyophilized sera of patients without radical prostatectomy with and without concentration (PSA in native serum corresponds to 100%)

| | Number of Samples n | Range of PSA values native sera ng/ml | % of Reconstituted PSA after Redilution | SD | Range min % | max % |
|---|---|---|---|---|---|---|
| PSA 1-fold (complete redilution) | 25 | 0.31–55.40 | 99.23 | 6.82 | 80.35 | 107.44 |
| PSA 2-fold (partial redilution) | 59 | 0.21–28.09 | 97.64 | 4.57 | 89.88 | 110.49 |
| PSA 3-fold (partial redilution) | 31 | 0.21–23.87 | 92.91 | 7.90 | 72.04 | 114.29 |
| PSA 3.5-fold (partial redilution) | 27 | 0.27–28.03 | 85.78 | 8.15 | 67.87 | 101.49 |
| PSA 4-fold (partial redilution) | 31 | 0.21–23.87 | 82.30 | 8.44 | 68.21 | 98.48 |

| Patient number | Native Abbott | PSA-value Hybritech | PSA-value Abbott | 2-fold Hybritech | PSA-value Abbott | 3-fold Hybritech | PSA-value Abbott | 4-fold Hybritech |
|---|---|---|---|---|---|---|---|---|
| 16 | 0.02 | 0.51 | 0.00 | 0.74 | 0.00 | 0.37 | 0.00 | 0.28 |
| 5 | 0.00 | 0.00 | 0.00 | 0.00 | 0.00 | 0.00 | 0.00 | 0.43 |
| 18 | 0.00 | 0.00 | 0.00 | 0.00 | 0.00 | 0.26 | 0.00 | 0.47 |
| n = 20 | x = 0.00 range 0.00 to 0.03 | x = 0.17 range 0.00 to 0.57 | x = 0.00 range 0.00 to 0.01 | x = 0.25 range 0.00 to 1.29 | x = 0.00 range 0.00 to 0.01 | x = 0.25 range 0.00 to 1.72 | x = 0.00 range 0.00 to 0.01 | x = 0.24 range 0.00 to 1.02 |

Interpretation according to definition:
Abbott IMX
20/20 in concentration negative
Hybritech Tandem E:
14/20 in concentration negative
5/20 in concentration suspicious
1/20 in concentration positive

EXAMPLE 6

The procedure of Example 1 is repeated and the following are results of PSA values after lyoconcentration in 83 patients after radical prostatectomy between 1/92 and 6/93 PSA-values are taken every 6 months.

| PSA values | No. of patients | No. of measurements |
|---|---|---|
| positive | 19 | 34 |
| suspicious | 11 | 11 |
| negative | 52 | 91 |
| Total | 82 | 126 |

Correlation of pathological results ("margin") with subsequent supersensitive detection of PSA

|  | PSA-value positive | PSA-value suspicious | PSA-value negative |
|---|---|---|---|
| Margin positive | 7 | 3 | 15 |
| Margin negative | 16 | 4 | 38 |

Conclusions

It can be seen from the above results that by using the process of the invention, sensitivity can be increased at least by a factor of 2 to 4. The increase is specific and grey area samples can be defined. In addition, the working procedure is extremely simple, using established, standard controls, calibrators, equipment and antibodies. Specially trained personal is not necessary. Results can be achieved quickly and the method can be combined with other supersensitive assays to increase sensitivity even further.

FIG. 1 shows a schematic representation of an apparatus useful for conducting the process of the present invention. It shows a drying apparatus 2, such as a freeze drier having a drying chamber and control equipment which is well known in the art. Such non-exclusively include a vacuum gauge, temperature controller, valves, vacuum pump, refrigerator, condenser tank, control units and so forth. A vessel 4 is disposed within the drying apparatus and may optionally be fitted with a closure such as a rubber stopper or cork 6. A quantity of serum 8 is deposited into the vessel 4. The vessel may rest on a container or support 7. Associated with vessel is an integrated scale or volume meter 10 which is connected to a calculator 16. Calculator 16 can stop the freeze drying process at a defined concentration, such as a 3-fold, 4-fold or 5-fold concentration or can provide for the addition of a calculated amount of distilled water after complete freeze drying to achieve the defined concentration, i.e. 3-fold, 4-fold or 5-fold concentration. The apparatus can include integrated vortex and/or heating means 12 to achieve a substantially complete mixture of the concentrated probe. An appropriate inlet/outlet 14 is provided for the insertion of serum or distilled water as required.

It is to be understood that various features of the individual embodiments may be combined and/or interchanged and need not be precisely employed as shown in this drawing to be within the scope of the invention. It is to be further understood that although we have shown the preferred forms of the invention, that various modifications may be made in the details thereof without departing from the spirit as comprehended from the following claims.

What is claimed is:

1. A process for the quantitative determination of the amount of prostate specific antigen in a sample of patient serum of a predetermined volume or weight, wherein the patient serum sample has a prostate specific antigen content of less than about 2 ng/ml which comprises subjecting the patient serum sample to a freeze drying concentration step, which concentration step reduces the water content thereof such that the concentrated sample consists essentially of patient serum and water, wherein the water content is reduced by at least 50%, analyzing the concentrated sample to determine the quantity of the antigen content thereof, and calculating back the quantity of the antigen of the original patient serum sample.

2. The process according to claim 1 wherein the antigen to be quantitatively determined is a prostate specific antigen and the patient serum sample has a prostate specific antigen content of less than about 1.2 ng/ml.

3. The process according to claim 1 wherein the analyzing conducted is an immunoassay.

4. The process according to claim 1 wherein the freeze drying concentration is conducted until 5 to 50% by volume of the original patient serum sample is attained.

5. The process according to claim 1 wherein the freeze concentration is conducted before or after a step comprising the elimination of solid materials in the serum.

6. The process according to claim 1 wherein the freeze concentration is conducted before or after a step comprising the elimination of human albumen in the serum.

7. The process of claim i wherein the sample is from a patient having undergone a radical prostatectomy.

8. A process for determining the quantity of prostate specific antigen in a patient sample having a prostate specific antigen content of less than about 2 ng/ml which comprises subjecting the sample to a freeze drying concentration step, which concentration step consists essentially of reducing the water content thereof by at least 50% such that the concentrated sample consists essentially of the prostate specific antigen and water, and then quantitatively analyzing the concentrated sample to determine the quantity of the prostate specific antigen therein.

9. The process of claim 8 comprising the subsequent step of calculating back the quantity of the substance in the biological sample before concentration.

* * * * *